United States Patent [19]

Gross

[11] Patent Number: 5,279,957
[45] Date of Patent: Jan. 18, 1994

[54] CDNA ENCODING HUMAN PHOSPHOLIPASE A$_2$ POLYPEPTIDE

[75] Inventor: Richard Gross, St. Louis, Mo.

[73] Assignee: Washington University, St. Louis, Mo.

[21] Appl. No.: 876,284

[22] Filed: Apr. 30, 1992

[51] Int. Cl.$^5$ .................... C12N 5/10; C12N 1/21; C12N 1/19; C12N 15/85

[52] U.S. Cl. .................... 435/240.2; 435/172.3; 435/252.31; 435/252.33; 435/252.3; 435/254.11; 435/320.1; 536/23.2

[58] Field of Search .................... 435/320.1, 69.1, 172.3, 435/252.31, 252.33, 252.3, 240.2, 256; 536/23.2; 935/9, 11

[56] References Cited

PUBLICATIONS

Davidson, et al., J. Mol. Evol. 31:228-238 (1990).
Clark, et al., Cell 65:1043-1051 (1991).
Sharp et al., J. Biol. Chem. 266:14850-14853 (1991).
Loeb, et al., J. Biol. Chem. 261:10467-10470 (1986).
Zupan, et al., FEBS 284:27-30 (1991).
Ichimura et al., Proc. Natl. Acad. Sci. U.S.A. 85:7084-7088 (1988).
Ford et al., Chapter 8, "Lipobiology" in Fundamentals of Medical Cell Biology, vol. 3A, pp. 225-256 (1992).
Dennis et al., FASEB, 5:2068-2077 (1991).
Dennis, Biotechnology, 5:1294-1300 (1987).
Wolf, et al., J. Biol. Chem. 260:7295-7303 (1985).
Lombardo, et al., J. Biol. Chem. 260:7234-7240 (1985).
Deems et al., Biochem. Biophys. Acta 917:258-268 (1987).
Young, et al. Proc. Natl. Acad. Sci. U.S.A. 80:1194-1198 (1983).
Kushner (1987) *Escherichia Coli and Salmonnella Typhimurium* vol. 2 ed. Neidhart PN J02111796-A (1990)*.
Isobe et al. (1991) *J. Mol. Biol.* vol. 217 pp. 125-132.
Nielsen (1991) *Biochimica et Biophysica Acta* vol. 1088 pp. 425-428.
Brandt et al. (1992) #Accession S18911*.
Adams et al. (1992) Nature 355, 632-634*.
Hazen et al. (1990) *J. Biol. Chem.* vol. 265(18) pp. 10622-10630*.
Hazen et al. (1991) *Biochem J.* vol. 280 pp. 581-587.
Hazen et al. (1992) *Circ Res. (U.S.)* 70(3) pp. 486-495*.
Ye et al. (1987) *J. Biol. Chem.* vol. 262 (No. 8) pp. 3718-3725.
Ichimura et al. (1987) *Febs Lett* vol. 219 (No. 1) pp. 79-82.
Murakami et al. (1992) *J. Biochem.* 111(2) pp. 175-181.
Kramer et al. (1991) *J. Biol. Chem* 266 (8) pp. 5268-5272.
Aarsman et al. (1989) *J. Biol. Chem* vol. 264 (No. 17) pp. 10008-10014.
Hirashima et al. (1992) *J. Neurochem.* vol. 59(2) pp. 708-714.*

*Primary Examiner*—Richard A. Schwartz
*Assistant Examiner*—Kathleen L. Choi
*Attorney, Agent, or Firm*—Woodcock Washburn Kurtz Mackiewicz & Norris

[57] ABSTRACT

The present invention provides a novel human polypeptide having phospholipase A$_2$ activity, referred to as PLA$_2$(Ca$^-$). The invention also provides nucleic acid sequences coding for the novel polypeptide, expression vectors comprising the nucleic acid sequences coding for the novel polypeptide, host cells and cell cultures capable of expressing the novel polypeptide. The present invention further provides antisense oligonucleotides for modulation of expression of the gene coding for the novel polypeptide. Assays for screening test compounds for their ability to inhibit phospholipase A$_2$ activity are also provided.

6 Claims, 2 Drawing Sheets

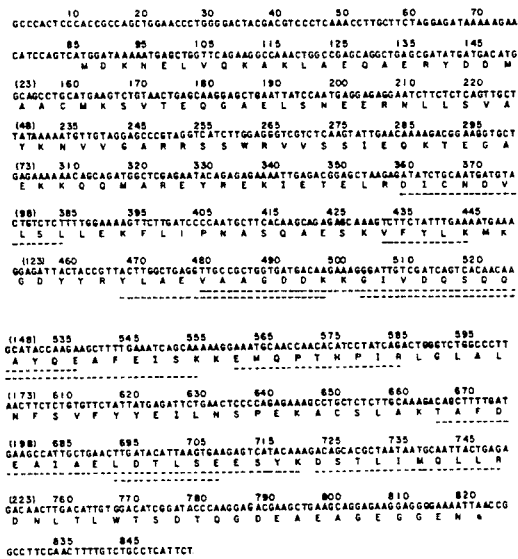

```
            10              20              30              40              50              60              70
      GCCCACTCCCACCGGCCAGCTGGAAACCCTGGGGACTACGACGTCCCTCAAACCTTGCTTCTAGGAGATAAAAAGAA
            85              95             105             115             125             135             145
      CATCCAGTCATGGATAAAAATGAGCTGGTTCAGAAGGCCAAACTGGCCGAGCAGGCTGAGCGATATGATGACATG
 (23)        160             170             180             190             200             210             220
      GCAGCCTGCATGAAGTCTGTAACTGAGCAAGGAGGCTGAGAATTATCCAATGAGGAGAGGAATCTTCTCTCAGTTGCT
       A  A  C  M  K  S  V  T  E  Q  G  A  E  L  S  N  E  E  R  N  L  S  V  A
 (48)        235             245             255             265             275             285             295
      TATAAAAATGTTGTAGGAGCCCGTAGGTCATCTTGGAGGGTCGTCTCAAGTATTGAACAAAAGACGGAAGGTGCT
       Y  K  N  V  V  G  A  R  R  S  S  W  R  V  V  S  S  I  E  Q  K  T  E  G  A
 (73)        310             320             330             340             350             360             370
      GAGAAAAACAGCAGATGGCTCGAGAATACAGAGAGAAAATTGAGACGGAGCTAAGAGATATCTGCAATGATGTA
       E  K  K  Q  Q  M  A  R  E  Y  R  E  K  I  E  T  E  L  R  D  I  C  N  D  V
 (98)        385             395             405             415             425             435             445
      CTGTCTCTTTTGGAAAAGTTCTTGATCCCCAATGCTTCACAAGCAGAGAGCAAAGTCTTCTATTTGAAAATGAAA
       L  S  L  L  E  K  F  L  I  P  N  A  S  Q  A  E  S  K  V  F  Y  L  K  M  K
(123)        460             470             480             490             500             510             520
      GGAGATTACTACCGTTACTTGGCTGAGGTTGCCGGTGATGACAAGAAAGGGATTGTCGATCAGTCACAACAA
       G  D  Y  Y  R  Y  L  A  E  V  A  G  D  D  K  K  G  I  V  D  Q  S  Q  Q
```

FIG. 1A

```
(148)   535         545         555         565         575         585         595
        GCATACCAAGAAGCTTTGAAATCAGCAAAAAGGAAATGCAACCAACACATCCTATCAGACTGGGTCTGGCCCTT
        A   Y   Q   E   A   F   E   I   S   K   K   E   M   Q   P   T   H   P   I   R   L   G   L   A   L (173)   610         620         630         640         650         660         670
        AACTTCTCTGTGTTCTATTATGAGATTCTGAACTCCCCAGAGAAAGCCTGCTCTCTTGCAAAGACAGCTTTTGAT
        N   F   S   V   F   Y   Y   E   I   L   N   S   P   E   K   A   C   S   L   A   K   T   A   F   D (198)   685         695         705         715         725         735         745
        GAAGCCATTGCTGAACTTGATACATTAAGTGAAGAGTCATACAAAGACAGCACGCTAATAATGCAATTACTGAGA
        E   A   I   A   E   L   D   T   L   S   E   E   S   Y   K   D   S   T   L   I   M   Q   L   L   R (223)   760         770         780         790         800         810         820
        GACAACTTGACATTGTGGACATCGGATACCCAAGGAGACGAAGCTGAAGGAGGAGAAGGAGGGGAAAATTAACCG
        D   N   L   T   L   W   T   S   D   T   Q   G   D   E   A   E   G   E   G   G   E   N   *

835         845
        GCCTTCCAACTTTTGTCTGCCCTCATTCT.
```

FIG. 1B

CDNA ENCODING HUMAN PHOSPHOLIPASE $A_2$ POLYPEPTIDE

ACKNOWLEDGEMENT OF GOVERNMENT SUPPORT

This invention was made with Government support under HL35864 awarded by NIH. The Government has certain rights in this invention.

FIELD OF THE INVENTION

The present invention relates to the field of polypeptides produced by recombinant DNA technology, more particularly the present invention relates to the field of polypeptides having phospholipase $A_2$ activity.

BACKGROUND OF THE INVENTION

Many lipids or lipid-derived products generated by phospholipases acting on phospholipids in membranes have been implicated as mediators and second messengers in signal transduction. Lipid-derived second messengers of signal transduction are typically short-lived lipid metabolites that are synthesized from membrane-derived lipid precursors in response to cell stimulation (e.g., ligand-receptor coupling, electrical stimulation, and elevation in intracellular calcium). The production of lipid-derived second messengers is initiated by the activation of intracellular phospholipases, which liberate metabolites capable of propagating a cell-specific cascade of biochemical events that collectively results in cell activation.

One such lipid second messenger is arachidonic acid which is found esterified in the sn-2 position of membrane phospholipids and can potentially be released by a number of phospholipases, although recent research points to phospholipase $A_2$ as the major mediator of arachidonic acid release, at least for prostaglandin and leukotriene biosynthesis. The other product of phospholipase $A_2$ action is lysophospholipid, a class of amphiphilic molecules that contribute to membrane regulation by virtue of their ability to alter membrane physical properties and also serve either as direct precursors of lipid second messengers (e.g., platelet activating factor) or are second messengers in their unmodified form. When the phospholipid is an alkyl ethercontaining phosphatidylcholine, the lysophospholipid upon acetylation forms platelet-activating factor (PAF), another lipid that is a potent cellular mediator.

Arachidonic acid mobilized from intracellular phospholipid storage depots in cellular membranes thus has multiple metabolic fates including: 1) internal oxidation, resulting in the generation of biologically active eicosanoids; 2) transacylation, resulting in the redistribution of arachidonic acid in phospholipid molecular species; 3) thioesterification, resulting in the subsequent reincorporation of released arachidonic acid into lipid metabolic pathways; or 4) secretion into the extracellular space, facilitating cell to cell communication.

Davidson and Dennis (1990) *J. Mol. Evol.* 31, 228-238 recently compared and aligned all of the known sequences of phospholipase $A_2$. Low molecular weight phospholipases $A_2$ sequenced to date are all considered to be secreted and are composed of a single polypeptide chain, about 120 amino acids long, containing 10-14 cysteines, all in disulfide pairs. These cysteines constitute the bulk of the sequence conservation between the mammalian, reptile and insect secreted enzymes. In addition, these phospholipases $A_2$ require $Ca^{+2}$ for activity and contain a conserved $Ca^{+2}$ binding loop, whereas the nearby catalytic site contains a histidine/aspartic acid pair conserved throughout. Two human low molecular weight phospholipases $A_2$ have been sequenced. One is from the pancreas and is similar to the venom phospholipases $A_2$ of the old-world cobras and kraits, except for the addition of an internal loop of five amino acids and the fact that it is produced as a proenzyme. The other sequenced human low molecular weight phospholipase $A_2$, originally isolated from platelets and synovial fluid, is similar to the venom phospholipases $A_2$ of old- and new-world snakes such as the diamondback rattlesnake. These sequences have an extended COOH terminus and a related but distinct disulfide bond pattern. Bee venom phospholipase $A_2$ shows a highly divergent sequence that is missing an $NH_2$-terminal section, but is homologous in other regions.

In order to fully appreciate the activity of phospholipase $A_2$ and its role in cellular communication and disease, much research has been done on extracellular secreted phospholipases $A_2$. Although these studies have provided valuable information, the contribution of intracellular phospholipase $A_2$ has not been well-studied. The single human non-low molecular weight phospholipase $A_2$ sequenced to date is an 85kD polypeptide which shares limited structural homology with protein kinase C, GAP, and phospholipase C, Clark et al. (1991) Cell 65, 1043-1051 and Sharp et al. (1991) J. Biol. chem. 266, 14850-14853. Other forms of intracellular phospholipase $A_2$ remain poorly characterized. Thus there continues to be a need for identification and characterization of new phospholipase $A_2$ enzymes.

SUMMARY OF THE INVENTION

The present invention provides a novel human polypeptide having phospholipase $A_2$ activity. Applicant has discovered a novel human polypeptide having phospholipase $A_2$ activity. The polypeptide discovered by Applicant has not heretofore been reported in humans and will be referred to hereinafter as $PLA_2(Ca^-)$. The novel polypeptide of the invention catalyzes the cleavage of the sn-2 fatty acid of choline and ethanolamine glycerophospholipids through the formation of a stable acyl-enzyme intermediate. Transesterification of the sn-2 acyl group of phosphatidylcholine to the recombinant 30 kDa polypeptide of the invention is over 50-fold selective for arachidonic acid, is augmented by calcium ion and results in the formation of an arachidonoyl-thioester intermediate.

The polypeptide of the invention is a novel intracellular, mammalian phospholipase $A_2$ that employs a catalytic strategy distinct from that utilized by extracellular phospholipases $A_2$ (i.e., formation of an acyl-enzyme intermediate by nucleophilic attack versus activation of a water molecule). The invention also provides nucleic acid sequences coding for the novel polypeptide, expression vectors comprising the nucleic acid sequences coding for the novel polypeptide, host cells and cell cultures capable of expressing the novel polypeptide. The invention additionally provides purified $PLA_2(Ca^-)$. The present invention further provides antisense oligonucleotides for modulation of expression of the gene coding for the novel polypeptide. Assays for screening test compounds for their ability to inhibit phospholipase $A_2$ activity are also provided.

This invention is more particularly pointed out in the appended claims and is described in its preferred embodiments in the following description.

BRIEF DESCRIPTION OF THE FIGURES

FIG. 1A and FIG. 1B shows nucleotide sequence and deduced amino acid sequence of the human placental cDNA sequence coding for the novel polypeptide of the invention. The sequence in FIG. 1A and FIG. 1B has 84 nucleotides present in the 5' non-translated region (SEQ ID NO: 1, bases 1-84), 735 bases of translated message corresponding to a polypeptide of 245 amino acids (SEQ ID NO: 1, bases 85-822) and 31 bases in the 3' non-translated region. Sequences of proteolytic peptides derived from sheep platelet phospholipase $A_2$ are shown by underlining. These proteolytic peptides were identical to the sequence deduced for the novel polypeptide of the invention in 81 of 82 amino acids, differing only in amino acid 219 where a glutamine for glutamate substitution was present in the polypeptide of the invention.

DETAILED DESCRIPTION OF THE INVENTION

The present invention provides a novel intracellular human phospholipase $A_2$ that employs a catalytic strategy distinct from that utilized by extracellular phospholipases $A_2$ (i.e., formation of an acyl-enzyme intermediate by nucleophilic attack versus activation of a water molecule). Fragments of $PLA_2(Ca^-)$ having phospholipase $A_2$ activity are also within the scope of the invention. The novel $PLA_2(Ca^-)$ of the invention catalyzes the cleavage of the sn-2 fatty acid of choline and ethanolamine glycerophospholipids through the formation of a stable acyl-enzyme intermediate. Transesterification of the sn-2 acyl group of phosphatidylcholine to the recombinant polypeptide is over 50-fold selective for arachidonic acid, is augmented by calcium ion and results in the formation of an arachidonoyl-thioester intermediate. The major phospholipase $A_2$ activity in sheep platelets is mediated by at least three chromatographically resolvable isoforms of a 60 kDa dimeric polypeptide (containing 30 kDa subunits) which are responsive to physiologic increments in calcium ion and possess a dramatic substrate selectivity (Loeb, L. A. and Gross, R. W. (1986) *J. Biol. Chem.* 261:10467-10470). Similar to the sheep platelet $PLA_2$'s, the $PLA_2$ of the present invention does not require calcium for activation.

Although calcium ion augmented the incorporation of arachidonic acid into recombinant protein, it was not an obligatory cofactor in the formation of the arachidonoylenzyme intermediate (i.e., the acylenzyme was formed in the presence of EGTA). These results are comparable to prior experimental findings utilizing sheep platelet phospholipase $A_2$ where calcium ion was found to be sufficient, but not necessary, for activation of this phospholipase $A_2$ (Zupan, L. A. Kruszka, K. K., and Gross, R. W. *FEBS* 284, 27-30 (1991)). $PLA_2(Ca^-)$ is presently believed to be expressed in platelets. Polyclonal antibodies prepared against purified sheep platelet $PLA_2$ cross-react with the $PLA_2$ found in human platelets.

One unifying biochemical mechanism present during signal transduction in the majority of mammalian cells is that arachidonic acid is released from endogenous phospholipid storage pools after ligand-receptor coupling. The concentration of free arachidonic acid in resting cells is small because the overwhelming majority of cellular arachidonic acid is covalently linked to the sn-2-position of phospholipid storage pools. However, during cellular activation the concentration of non-esterified arachidonic acid is dramatically increased by intracellular phospholipases.

Released arachidonic acid is rapidly oxygenated by one of several oxidative enzymes (e.g. cyclooxygenase or lipoxygenase) to initiate an enzymatic cascade that results in the generation of a multiplicity of different oxygenated metabolites of arachidonic acid (e.g. eicosanoids). Eicosanoids are a family of oxygenated arachidonic acid derivatives that interact with specific cellular receptors to amplify and propagate the flow of biological information. Because the eicosanoid-producing oxidative enzymes can not oxygenate esterified arachidonic acid present in phospholipids, arachidonic acid is biologically inactive until it is released from endogenous phospholipids by intracellular phospholipases. Furthermore, because the release of arachidonic acid from endogenous membrane stores by phospholipases is the rate-limiting step in eicosanoid production it is clear that the extent of phospholipase activation represents a primary biochemical determinant of the magnitude and type of each cell's response to stimulation. Since the Km of arachidonic acid for either cyclooxygenase or lipoxygenase is well above the concentration of free arachidonic acid in resting cells, the potential for the rapid catalytic amplification of a single chemical stimulus by the activation of phospholipase is inherent in the design of this signal transduction system.

After arachidonic acid is released from endogenous phospholipid stores, a highly specific cascade of enzyme-related reactions is initiated, which leads to the production of structurally related metabolites (eicosanoids) that have separate and distinct biological functions. These oxygenated eicosanoids are highly lipid soluble and thus they readily traverse cellular membranes, facilitating their interaction with receptors on adjacent cells or with receptors in their cell of origin.

Arachidonic acid may be released directly by the action of phospholipase $A_2$ or by sequential enzymic reactions initiated by phospholipase $A_1$, C or D. Recent work has demonstrated that arachidonic acid released during cell stimulation typically results from activation of at least two types of phospholipase activities, phospholipase $A_2$ and phospholipase C. For example, platelet activation by thrombin results in the highly selective release of arachidonic acid from endogenous phospholipids that is accompanied by the concomitant accumulation of lysophospholipids, diglycerides and phosphatidic acid.

A wide variety of cells produce platelet-activating factor (PAF) when stimulated, including, but not limited to, platelets, basophils, neutrophils, macrophages, and endothelial cells. An essential biochemical requirement for the production of PAF is the ability of PAF-producing cells to contain the enzymic machinery necessary to synthesize the 1-O-alkyl bond. Two predominant mechanisms for PAF biosynthesis occur in mammalian cells. The first pathway is initiated by phospholipase $A_2$ hydrolysis of 1-O-alkyl-2-acyl-sn-glycerol-3-phosphocholine (alkyl acyl GPC) followed by acetylation of lyso-PAF. The second pathway involves acetylation of 1-O-alkyl-2-lyso-sn-glycerol-3-phosphate followed by dephosphorylation to yield 1-O-alkyl-2-acetyl-sn-glycerol. This moiety subsequently condenses with CDP choline to produce PAF.

Platelet activation by thrombin or collagen results in PAF synthesis. Subsequent interaction of PAF with its plasma membrane receptor induces serotonin release from intracellular granules and platelet aggregation. PAF also modulates neutrophil degranulation, phagocytosis, exocytosis, chemotaxis, and superoxide production. Macrophage phagocytosis of zymosan particles, antibody-coated erythrocytes and immune complexes is accompanied by PAF production that modulates a variety of subsequent macrophagemediated events.

PAF is also a lipid mediator of anaphylactic responses. PAF produced by anti-IgE challenges of IgE-sensitized basophils results in degranulation and histamine release. PAF can induce rapid and shallow breathing, transient apnea, and pulmonary edema in the respiratory system. In the cardiovascular system, PAF directly induces bradycardia hypotension, elevated right ventricular pressure, vascular spasms and increased vascular permeability.

PAF also has potent effects on many other biological systems. For example, PAF induces hepatic phosphoinositide turnover and glycogenolysis, which is accompanied by glucose release into the plasma. PAF has also been implicated as a mediator of ischemic bowel necrosis because it can independently induce lesions that are morphologically similar to those present during human necrotizing enterocolitis. Additionally, the role of PAF or a PAF-like lipid as an endogenous antihypertensive substance is currently under intense experimental scrutiny.

Nucleic acid sequences coding for the novel phospholipase $A_2$ of the invention may be obtained from human tissue. Although the nucleic acid sequences coding for PLA$_2$(Ca$^-$) have been initially isolated from cDNA libraries prepared from human placenta, the nucleic acid sequences coding for PLA$_2$(Ca$^-$) can also be isolated from genomic DNA and other human cDNA libraries.

At the present time, several nucleic acid sequences coding for PLA$_2$(Ca$^-$) have been discovered in human tissue (one of which has been fully sequenced (SEQ ID NO: 1), the others partially characterized, SEQ ID NO: 3 and SEQ ID NO: 4). Due to natural allelic variation or the presence of isoforms of this activity, other variants of PLA$_2$(Ca$^-$) may also be present in human tissue. Accordingly, any and all such natural variants of PLA$_2$(Ca$^-$) are within the scope of the present invention.

Fragments of the nucleic acid sequence of the invention coding for portions of PLA$_2$(Ca$^-$) having phospholipase $A_2$ activity are also within the scope of the invention. Phospholipase $A_2$ activity refers to the ability to cleave arachidonic acid from a phospholipid, preferably from the sn-2 position and/or facilitate the subsequent release of fatty acid to other nucleophilic acceptors, e.g. water (phospholipase), lipids (transacylase) or protein (e.g. cyclooxygenase or lipoxygenase).

The nucleic acid sequences of the invention may also contain linker sequences, restriction endonuclease sites and other sequences useful for cloning, expression or purification of PLA$_2$(Ca$^-$) or fragments thereof.

Another aspect of the present invention provides expression vectors, host cells transformed to express the nucleic acid sequences of the invention, and cell cultures capable of expressing the nucleic acid sequences of the invention. Nucleic acid coding for PLA$_2$(Ca$^-$) or at least one fragment thereof may be expressed in prokaryotic or eukaryotic host cells, including bacterial cells such as *E. coli, Bacillus subtilis* and other enterobacteriaceae such as *Salmonella typhimurium* or *Serratia marcescens*, insect cells such as *Spodoptera frugiperda*, yeast cells such as *Saccharomyces cerevisiae*, or mammalian cells such as Chinese hamster ovary cells (CHO), COS-7 or MDCK cells. The foregoing list is illustrative only and is not intended in any way to limit the types of host cells suitable for expression of the nucleic acid sequences of the invention. As used herein, expression vectors refers to any type of vector that can be manipulated to contain a nucleic acid sequence coding for PLA$_2$(Ca$^-$) or at least one fragment thereof, such as plasmid expression vectors and viral vectors. In any particular embodiment of the invention, the expression vector is selected to be compatible with the desired host cell so that expression of the nucleic acid coding for PLA$_2$(Ca$^-$) or fragment thereof will be achieved. Plasmid expression vectors preferably comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Most commonly used are the genes coding for ampicillin, tetracycline, chloramphenicol, or kanamycin resistance. Suitable expression vectors, promoters, enhancers, and other expression control elements are known in the art and may be found, for example, in Sambrook et al. *Molecular Cloning: A Laboratory Manual*, second edition, Cold Spring Harbor Laboratory Press, Cold Spring Harbor, N.Y., 1989. For example, for expression in *E. coli*, plasmids such as pBR322, pUC18, and pUC19 may be used. For expression in *S. cerevisiae* plasmids such as YRp7 may be employed. See, for example, U.S. Pat. No. 4,766,075 for other plasmids and methods for expression of foreign genes in yeast cells. For expression in mammalian cells, plasmids such as pMT2 and pMSG may be employed. Expression in yeast, insect or mammalian cells would lead to partial or complete glycosylation of the recombinant material and formation of any inter- or intrachain disulfide bonds, if such exist. Suitable viral vectors include baculovirus (see U.S. Pats. Nos. 4,745,051 and 4,879,236, and Summers and Smith "Manual of Methods for Baculovirus Vectors and Insect Cell Culture Procedures", 2nd edition, *Texas Agricultural Station Bulletin No.* 15555, Texas Agricultural Experiment Station, College Station, Tex.), Vaccinia virus (Mackett et al (1985) *DNA Cloning: A Practical Approach*, D. M. Glover, ed., vol. 2, p. 191, IRL Press, Oxford, England), and adenovirus (Berkner, K. L. (1988) *BioTechniques* 6: 616). A preferred expression vector is baculovirus.

If PLA$_2$(Ca$^-$) or fragment thereof is expressed as a fusion protein, it is particularly advantageous to introduce an enzymatic cleavage site at the fusion junction between the carrier protein and PLA$_2$(Ca$^-$) or fragment thereof. PLA$_2$(Ca$^-$) or fragment thereof may then be recovered from the fusion protein through enzymatic cleavage at the fusion site and biochemical purification using conventional techniques for purification of proteins and peptides.

Depending on the type of expression vector employed, host cells can be transformed to express the nucleic acid sequences of the invention using conventional techniques such as calcium phosphate or calcium chloride co-precipitation, DEAE-dextran-mediated transfection, or electroporation. The term transformed, as used herein refers to the incorporation of an expression vector containing the nucleic acid sequence coding for PLA$_2$(Ca$^-$) or at least one fragment thereof into a host cell by any method including infection in the case of viral vectors. Suitable methods for transforming the host cells are well-known and may be found in Sambrook et al., *Molecular Cloning: A Laboratory Manual*, second edition, Cold Spring Harbor Laboratory Press, Cold Spring Harbor, N.Y., 1989, and other laboratory textbooks. The transformed host cells thus form cell cultures capable of expressing PLA$_2$(Ca$^-$) or at least one fragment thereof. The nucleic acid sequences of the invention may also be synthesized using standard techniques.

The host cells are then cultured in an appropriate medium to produce a mixture of cells and medium containing the phospholipase A$_2$ (Ca$^-$) or fragment thereof. Optionally, the mixture may be purified to produce purified phospholipase A$_2$ (Ca$^-$) or fragment thereof. The terms "purified" and "isolated" are used interchangeably herein and, when used to describe the state of PLA$^2$(Ca$^-$) produced by the invention, refers to PLA$_2$(Ca$^-$) substantially free of protein or other materials normally associated with PLA$_2$(Ca$^-$) when produced by non-recombinant cells, i.e. in its "native state". "Substantially" refers to greater than about 50% purity of PLA$_2$(Ca$^-$), i.e. PLA$_2$(Ca$^-$) is present in a mixture of PLA$_2$(Ca$^-$) and other material in an amount greater than about 50% of the mixture. It is to be understood, that the level of purity of PLA$_2$(Ca$^-$) is not critical to the activity or usefulness of the polypeptide of the invention. For example, when produced in *E. coli*, PLA$_2$(Ca$^-$) is present in the membrane fraction and can be used without purification. Thus purification of the polypeptide is not required for its use in assays. Suitable purification methods include ion exchange chromatography, affinity chromatography, electrophoresis and other conventional methods for purification of proteins. See, for example, Scopes, *Protein Purification, Principles and Practice*, second edition, Springer-Verlag, New York, 1987 for these and other suitable methods for purification of the PLA$_2$(Ca$^-$) protein and fragments thereof.

Another aspect of the invention provides antisense oligonucleotides capable of inhibiting expression of the nucleic acid sequence coding for PLA$_2$(Ca$^-$). The oligonucleotides of the invention are preferably from about 10 to about 50 bases in length, more preferably from about 12 to about 30 bases in length, most preferably from about 15 to about 25 bases in length. Oligonucleotides may be selected from any portion of the complementary sequence of the nucleic acid sequence coding for PLA$_2$(Ca$^-$) (SEQ ID NO: 1). Preferably, however, the oligonucleotides comprise sequences complementary to the 5' end of the coding sequence which may also include sequences complementary to the 3' end of the promoter for this gene. Selected sequences of the nucleic acid sequence coding for PLA$_2$(Ca$^-$) can be tested for activity, e.g., by contacting cells capable of expressing PLA$_2$(Ca$^-$) with the oligonucleotide under conditions appropriate for passage of the nucleic acid sequence into the cells, and determining the presence of PLA$_2$(Ca$^-$) or PLA$_2$(Ca$^-$) activity in the cells. If expression of the gene coding for PLA$_2$(Ca$^-$) has been inhibited by the oligonucleotide, PLA$_2$(Ca$^-$) or PLA$_2$(Ca$^-$) activity in the cells will be less than that present in control cells not exposed to the oligonucleotide.

The antisense oligonucleotide sequences can be DNA or RNA. Both types are referred to herein as oligonucleotides. The oligonucleotides can be chemically synthesized using known techniques or produced using recombinant DNA techniques. The oligonucleotides of the invention can be modified at a variety of locations along their length. For example, they can be modified by the addition of groups at the 5' end, the 3' end or both, as well as on the internal phosphate groups or on the bases. Whether oligonucleotides to be used are modified, and, if so, the location and extent of modification will be determined, for example, by the desired effect on gene expression, uptake of the oligonucleotides into cells, and inhibition of degradation of the oligonucleotides once they are inside cells. For example, if the desired effect is increased uptake of the oligonucleotide into cells, modification of the oligonucleotide by addition of a lipophilic group at the 5' end would be beneficial. Uptake of the oligonucleotides into cells can also be increased by linkage to a protein which interacts with receptors or antigenic sites on the surface of the cell as described in U.S. Pat. No. 4, 587,044. Modification of oligonucleotides can also be carried out by the addition of an intercalating agent such as an acridine dye at 5' or 3' ends of the oligonucleotides, on bases, or on internucleophosphate groups. Modification in this manner may result in stronger bonding between the oligonucleotides of the invention and the target complementary sequence of the gene. Modification of the internal phosphate groups or backbone of the oligonucleotide can be accomplished in a variety of ways such as alkyl or aryl phosphonate linkage of bases described in U.S. Pat. No. 4,469,863, phosphorothioate linkage of bases, formacetal linkage as described in Matteucci, M. (1990) Tetrahedron Letters 31, 2385-2388. This list is exemplary only and is not intended to limit in any way the types of modifications of the oligonucleotides that are useful in the present invention.

A further aspect of the invention provides methods of inhibiting PLA$_2$(Ca$^-$) expression comprising contacting cells with a nucleic acid sequence complementary to one or more regions of the PLA$_2$(Ca$^-$) gene and capable of hybridizing with one or more regions of the PLA$_2$(Ca$^-$) gene, under conditions appropriate for passage of the nucleic acid sequence into the cells. Preferred cells are human cells.

For in vivo uses, it is generally preferred to apply the oligonucleotides of the invention internally such as orally, intravenously, parenterally or intramuscularly. Other forms of administration, such as transdermal or topical may also be useful. Oligonucleotides are preferably administered in combination with a pharmaceutically acceptable carrier or diluent such as saline or a buffer. The oligonucleotides may also be mixed with liposomes or other carriers. For in vitro use, the oligonucleotides are generally in a suitable buffer.

The PLA$_2$(Ca$^-$) is also useful as an antigen for preparation of polyclonal and/or monoclonal antibodies. Such antibodies can be prepared using standard techniques, such as the methods in Harlow and Lane, *Antibodies, A Laboratory Manual*, Cold Spring Harbor Laboratory, Cold Spring Harbor, N.Y. 1988.

PLA$_2$(Ca$^-$) of the invention is additionally useful in screening assays for identification of compounds capable of inhibiting PLA$_2$(Ca$^-$) which are expected to be useful as an anti-platelet therapeutic or in treating conditions or their sequelae linked to the release of arachidonic acid and the synthesis of eicosanoids, as discussed herein, such as myocardial infarction, autoimmune disease, allergy, atherosclerosis and inflammation. Accordingly, the present invention provides a method for identifying compounds capable of inhibiting PLA$_2$(Ca$^-$) comprising contacting PLA$_2$(Ca$^-$) with a arachidonic acid moiety; and determining arachidonic acid incorporation into PLA$_2$(Ca$^-$) and/or the release of arachidonic acid to other nucleophilic acceptors as detailed previously.

PLA$_2$(Ca$^-$) of the invention can be substituted for other PLA$_2$'s in assays designed to test PLA$_2$ activity such as, for example, the assay disclosed herein in the Examples or in Wolf and Gross (1985) *J. Biol. Chem.* 260, 7295-7303 and modifications thereof. The PLA$_2$(Ca$^-$) of the invention can be substituted for other PLA$_2$'s in screening assays to identify compounds having PLA$_2$ inhibitory or activating activity such as, for example, the assay described herein in the Examples or Lombardo and Dennis (1985) *J. Biol. Chem.* 260, 7234-7240 or Deems et al. (1987) *Biochem. Biol. Acta* 917, 258-268. PLA$_2$ inhibitory activity refers to the ability of a compound to inhibit the cleavage of arachidonic acid from a phospholipid by PLA$_2$, preferably from the sn-2 position of a phospholipid. Conversely, PLA$_2$ activating activity refers to the ability of a compound to stimulate or increase the rate of cleavage of arachidonic acid from a phospholipid by PLA$_2$, preferably from the sn-2 position of a phospholipid.

Further, the nucleic acid sequence of the invention can be used in nucleic acid hybridization assays for detection of RNA or DNA coding for PLA$_2$(Ca$^-$) or closely related isoforms of this polypeptide in human tissue according to methods known in the art.

EXAMPLES

Cloning Of cDNA Sequence Coding For PLA$_2$(Ca$^-$) Antibody Production

Sheep platelet phospholipase A$_2$ was purified to apparent homogeneity according to the method of Loeb, L. A., and Gross, R. W. (1986) *J. Biol. Chem.* 261, 10467-10470 and injected intradermally into rabbits. The serum of one of fourteen rabbits evaluated contained a high affinity antibody (1:10,000 titer by ELISA) which recognized a predominant immunoreactive band at 30 kD (i.e., sheep platelet PLA$_2$) after Western blotting. The polyclonal antibody was purified by ion exchange chromatography according to the method of Bruck, D., Portetelle, D., Glineur, C., and Bollen A. (1982) *J. Immunol. Methods* 53, 313-319 and the resultant salt eluate was subsequently "cleared" by incubation with *E. coli* lysate.

cDNA Cloning

A human placental λgt11 cDNA library as disclosed in Ye, R. D., Wun, T., and Sadler, J. E. (1987) *J. Biol. Chem.* 262, 3718-3725 was kindly provided by Dr. E. Sadler (Washington University, St. Louis, Mo.). Expression screening of 2.6×10$^6$ plaques with antibody directed against sheep platelet phospholipase A$_2$ described in 1. led to the identification of eight positive clones. Secondary screening was performed by identification of clones which produced a β-gal fusion protein capable of serving as antigen to affinity purified antibody directed against sheep platelet phospholipase A$_2$ according to the method of Young and Davis (1983) *Proc. Natl Acad. Sci. USA* 80, 1194-1198. Homogenates of isopropyl-β-thiogalactopyranoside (IPTG) induced clones were blotted onto nitrocellulose paper, incubated with polyclonal antibody to sheep platelet phospholipase A$_2$, exhaustively washed and bound antibody was eluted by exposure to acidic buffer. The bound and subsequently eluted antibody was neutralized prior to its utilization as screening reagent by Western blotting of nitrocellulose strips containing bound authentic purified sheep platelet phospholipase A$_2$. Homogenates from a single clone (termed Clone D) were able to bind polyclonal antibody produced against sheep platelet phospholipase A$_2$ fusion protein and release it during exposure to acidic buffer culminating in a positive Western blot with authentic sheep platelet phospholipase A$_2$ Sanger dideoxy sequencing of the single positive clone isolated after secondary screening (clone D) demonstrated that it contained an open reading frame which was insufficient to encode the entire 30 kDa polypeptide (clone D corresponds in part to residues 426-855 in FIG. 1A and FIG. 1B SEQ ID NO: 1). Accordingly, the insert in clone D was labeled by random hexamer priming according to the method of Feinberg, A. P. and Vogelstein, B. (1983) *Anal. Biochem.* 132, 6-13 and was utilized to rescreen the placental λgt11 cDNA library. Rescreening of the placental λgt111 cDNA library was performed by oligonucleotide screening with the random hexamer labelled probe. This led to the identification of an additional twelve positive clones which were selected for "completeness" through hybridization with an oligonucleotide probe corresponding to the 5' end of clone D (CAAAGTCTTCTATTTGAA)(SEQ ID NO: 7). Of the four clones which hybridized to the 5, end of clone D, only one (termed clone 38) contained the entire coding region. All sequences were confirmed from independent clones and/or sequencing of complementary strands.

The composite cDNA sequence assembled from overlapping cDNA clones is shown in FIG. 1A and FIG. 1B (SEQ ID NO: 1) with the deduced amino acid sequence below. A total of 2834 nucleotides were present with 84 nucleotides in the 5' non-translated region, 735 residues of translated message corresponding to a polypeptide of 245 residues (calculated M$_r$=27745) and 2015 bases in the 3' nontranslated region. The coding portion of the protein begins at base 85 with methionine and ends with TAA at base 822.

The deduced amino acid sequence of this human intracellular phospholipase A$_2$ contained an open reading frame comprised of 245 residues (calculated M$_r$=27745) which was preceded by a typical Kozak initiation sequence (GTCATGG) and was terminated by a TAA stop codon. Inframe stop codons were present in both the 5' and 3' non-coding regions.

EXPRESSION OF DNA SEQUENCE CODING FOR PLA$_2$(Ca$^-$)

The cDNA insert coding for the full-length PLA$_2$(Ca$^-$) was excised from λgt11 with EcoRI and cloned into pUC18 (Life Technologies, Inc., Grand Island, N.Y.) at the EcoRI site. These were amplified by polymerase chain reaction (PCR) utilizing primers which introduced an Nco I restriction site flanking the 5' end and a BspMI restriction site (containing a Hind III compatible sequence) flanking the 3' end. The primers used had the following sequences:
TTCTGAATTCAGGAAACAGACCATG-
GATAAAAATGAGCTGGTT (SEQ ID NO: 5)

(the underlined portion is the NcoI site, and the 5' coding portion begins at SEQ ID NO: 5, base 22)
AAGAGAATTCAGCTGGAAGCAGGTT-TAATTTTCCCCTCCTTCTCC (SEQ ID NO: 6)
(the underlined portion is the BspMI site and the end of the coding region (3') begins at SEQ ID NO: 6, base 25)

Polymerase chain reaction was performed according to the method of Saiki et al. (1988) Science 238, 487–491. Subsequent restriction digestion with NcoI and BspMI resulted in the generation of a 752 BP fragment containing the entire coding sequence with Nco I and Hind III cohesive ends. Next, pMON 5842 (Monsanto Co., Chesterfield, Missouri) was digested with Nco I and Hind III restriction enzymes prior to the subsequent ligation of the coding sequence into the adapted pMON 5842. The structural integrity of the coding sequence was verified by Sanger dideoxy nucleotide sequencing. pMON 5842 contains the isopropyl-$\beta$-thio-galactopyranoside (IPTG)-inducible ptac promoter with g10L leader sequence.

E. coli DH5$\alpha$F'IQ cells (Life Technologies, Inc., Grand Island, N.Y.) were transformed with recombinant plasmid and incubated overnight in LB medium (Difco Laboratories, Detroit, Michigan) containing spectinomycin (Sigma, St. Louis, Mo.) (20 ug/ml). Recombinant PLA$_2$(Ca$^-$) was subsequently induced by incubation with 2 mM IPTG for thirty minutes.

Cells were pelleted by centrifugation at 750 xg$_{max}$ resuspended in buffer (50 mM Tris-Cl, pH 7.0, containing 1 mM EGTA, 10% glycerol and 0.25M dextrose), sonicated for one 20 second burst and centrifuged at 175,000 xg$_{max}$ for thirty minutes to separate the cytosolic and membrane fractions.

The membrane and cytosolic fractions were separated by SDS-PAGE. Transformation of E. coli and induction of recombinant PLA$_2$(Ca$^-$) by incubation with IPTG resulted in the de novo appearance of immunoreactive protein migrating at 30 KDa which was predominantly present in the membrane fraction. The de novo appearance of a polypeptide in transformed E. coli precisely corresponded to the molecular mass of sheep platelet phospholipase A$_2$. The 30 kDa recombinant polypeptide was recognized by antibody generated against purified sheep platelet phospholipase A$_2$.

Analysis Of Recombinant PLA$_2$(Ca$^-$)

Both the purified sheep platelet phospholipase A$_2$ and the recombinant protein were digested with trypsin and the resulting peptides were subjected to Edman degradation. The sequences of nine peptides derived from proteolysis of homogeneous sheep platelet phospholipase A$_2$ and subsequent Edman degradation were contained in the deduced amino acid sequence derived from Clone 38 which contained the entire coding sequence for PLA$_2$(Ca$^-$). (The peptides are shown underlined in FIG. 1A and FIG. 1B).

PLA$_2$(Ca$^-$) was found to have a molecular weight of about 30 kDa. The polypeptide was highly charged, containing 13% basic residues and 18% acidic residues which was consistent with its observed isoelectric point of 4.8. A hydropathy plot did not reveal any extended regions of hydrophobicity which could serve either as a signal polypeptide or as a transmembrane domain. Northern analysis of human placental mRNA demonstrated a single major band at 2.9 kb.

Homology searches demonstrated that 30 kDa PLA$_2$(Ca$^-$) possesses 73% homology to the $\eta$ chain of the 14-3-3 protein, a brain-specific dimeric protein having a molecular weight of about 55 kDa believed to have a function in monoamine biosynthesis because of its ability to activate tryosine hydroxylase and tryptophan hydroxylase, Ichimura et al. (1988) Proc. Natl. Acad. Sci. U.S.A. 85, 7084–7088. Homology between the tryptic peptides derived from sheep platelet phospholipase A$_2$ and the deduced human amino acid sequence of PLA$_2$(Ca$^-$) was considerably more extensive (matches between 81 of 82 amino acids) than that present between bovine 14-3-3 protein and human phospholipase A$_2$. These results suggest that the clone described herein represents a distinct gene product. No extended regions of significant homology between the PLA$_2$(Ca$^-$) coding sequence and other previously reported extracellular or intracellular phospholipase were found. Subsequent screening of a human EMBL-3 genomic library (Clontech, Palo Alto, Calif.) demonstrated the presence of at least three different genes. Partial sequences of two of these genes are shown in SEQ ID NO: 3 and SEQ ID NO: 4.

Activity Of PLA$_2$(Ca$^-$) Identification of Acyl-Enzyme Intermediates. Membranes derived from wild type (untransformed) or recombinant E. coli (PLA$_2$(Ca$^-$) is found in the membrane fraction) were incubated with 1-palmitoyl-2-[1-$^{14}$C]-arachidonoyl-sn-glycero-3-phosphocholine ($\sim$50 uM, specific activity = 110,000 dpm/nmol (dpm-disintegrations per min) in buffer (100 mM Tris-Cl, pH 7.5) containing either 10 mM CaCl$_2$ or 2 mM EGTA as indicated) for three minutes and immediately mixed with an equal volume of SDS sample buffer (60 mM Tris Cl (pH 6.8) 10% Glycerol, 10% SDS, Bromphenol Blue) prior to heating at 90° C. for three minutes. Subsequently, proteins were separated by SDS-PAGE employing 12% acrylamide gels, the gels were dried under vacuum and polypeptides containing radiolabel were visualized by fluorography according to the method of Hazen, S. L. and Gross, R. W. (1991) J. Biol. Chem. 266, 14526–14534. In this system, unincorporated lipids migrate as mixed micelles with SDS at the dye front which was eluted off the gel prior to the termination of electrophoresis.

SDS-PAGE and fluorography demonstrated a predominant band at 30 kDa in recombinant, but not wild type, E. coli. Exhaustive extraction of radiolabeled recombinant membranes with butanol did not remove radioactivity comigrating with the 30 kDa recombinant polypeptide. Preincubation of recombinant membranes with the thiol-specific reagent 5,5' dithiobisnitrobenzoic acid (DTNB), or the thiol-selective reagent N-ethylmaleimide ablated incorporation of [$^{14}$C] arachidonic acid in phosphatidylcholine into the recombinant polypeptide.

To characterize the nature of the association of [$^{14}$C] arachidonic acid and the recombinant polypeptide, recombinant membranes preincubated with [$^{14}$C] arachidonyl phosphatidyl-choline were quenched with SDS sample buffer prior to subsequent incubation with 1M NH$_2$OH, 1N NaOH, or 6N HCl for 60 min. Exposure to hydroxylamine resulted in the loss of approximately 70% of [$^{14}$C] arachidonic acid with nearly complete release of radiolabel manifest after treatment with acid or base. Collectively, these results demonstrate that [$^{14}$C] arachidonic acid was covalently bound to recombinant PLA$_2$(Ca$^-$) through a thioester linkage.

To examine the substrate selectivity of recombinant PLA$_2$(Ca$^-$), membranes derived from transformed *E. coli* were incubated with either 1-palmitoyl-2-[1-$^{14}$C]-archidonoyl-sn-glycero-3phosphoethanolamine, 1-palmitoyl-2-[1-$^{14}$C]-oleoyl-sn-glycero-3-phosphocholine or 1-palmitoyl-2-[1-$^{14}$C]-arachidonoyl-sn-glycero-3-phosphocholine and the covalent incorporation of the sn-2 fatty acid into the recombinant protein was quantified after SDS-PAGE and fluorography. Incorporation of radiolabeled sn-2 fatty acid was highly selective for arachidonic acid with only diminutive amounts of radioactivity incorporated utilizing phosphatidyl-choline containing oleic acid at the sn-2 position. Phosphatidylethanolamine was the preferred donor of arachidonic acid in direct comparisons to phosphatidylcholine, a result which paralleled the observed substrate selectivity of sheep platelet phospholipase A$_2$ (Zupan, L. A. Kruszka, K. K., and Gross, R. W. (1991) FEBS 284, 27-30). Furthermore, although calcium ion augmented the incorporation of arachidonic acid into recombinant protein, it was not an obligatory cofactor in the formation of the arachidonoyl-enzyme intermediate (i.e., the acylenzyme was formed in the presence of EGTA). These results are comparable to prior experimental findings utilizing sheep platelet phospholipase A$_2$ where calcium ion was found to be sufficient, but not necessary, for activation of this phospholipase A$_2$, (Zupan, L. A. Kruszka, K. K., and Gross, R. W. (1991) FEBS 284, 27-30). Calcium ion bound with high affinity to recombinant protein as ascertained by $^{45}$Ca$^{2+}$ blotting of the recombinant polypeptide. Calcium blotting was performed as described in Maruymura, K. Mikawa, T., and Ebashi, S. (1984) *J. Biochem.* 95, 511-519.

In contrast to results obtained with the 30 kDa protein isolated from sheep platelets, recombinant 30 kDa protein did not release covalently bound arachidonic acid suggesting that additional cofactors, covalent modification, formation of appropriate heterodimers or alternative modes of protein folding are necessary to induce the recombinant protein to release thioesterified arachidonic acid.

The results presented herein demonstrate a previously unanticipated level of complexity in both the chemical mechanism underlying the release of arachidonic acid by intracellular phospholipase A$_2$ and in the biologic diversity of the cellular constituents participating in arachidonic acid mobilization. The isolation of an arachidonoyl-enzyme intermediate demonstrates the potential of the thioesterified arachidonic acid to be specifically transferred to putative nucleophilic acceptors including H$_2$O (i.e., phospholipase A$_2$ activity), lipids (i.e., transacylase activity), proteins in oxidative cascades (e.g., cyclooxygenase or lipoxygenase) or proteins which facilitate the spatial translocation of arachidonic acid (i.e., the release of arachidonic acid to adjacent cells). The advantage that this catalytic strategy affords is the preservation of the negative free energy present in the ester bond of cellular phospholipids which allows the specificity inherent in protein-protein interactions to target individual cellular proteins, lipids or subcellular domains without an obligatory dependence on the random diffusion of released arachidonic acid. Insofar as the intermediate isolated in the present study is stable within mammalian cells (i.e., lifetimes >10$^{-6}$s), the potential for this family of phospholipases A$_2$ to serve as directors of arachidonic acid trafficking within cells seems evident.

The activation of intracellular phospholipase A$_2$ has traditionally been considered a concerted process initiated by the activation of an adjacent H$_2$O molecule in the active site of the enzyme. The results of the present study demonstrate that at least one intracellular phospholipase A$_2$ activity is mediated by a sequential process which is fundamentally distinct from the catalytic strategy employed by the extracellular phospholipase A$_2$. The genetic diversity present in this family of proteins and the catalytic strategy which they exploit underscore the complexity present in the orchestration of arachidonic acid mobilization during signal transduction in mammalian cells.

ASSAY FOR TESTING COMPOUNDS FOR PLA$_2$(Ca$^-$) INHIBITORY ACTIVITY

This assay measures the transfer of a radiolabeled arachidonic group from phosphatidylcholine to PLA$_2$(Ca$^-$). The PLA$_2$(Ca$^-$) will be incubated with phosphatidylcholine radiolabeled with tritium in the sn-2 arachidonic acid and various concentrations of the test compound in a diluent. The incubation will be terminated by cold, sodium dodecyl sulphate, or the addition of excess unlabeled phosphatidylcholine. The reaction mixture will be incubated with antibody directed against PLA$_2$(Ca$^-$), and then incubated with Scintillation Proximity Assay Beads (Amersham, Arlington Heights, Ill.) coupled to either Protein A or to anti-IgG, which will bind to the anti-PLA$_2$(Ca$^-$) antibody, in accordancewith the manufacturer's instructions. Antibody to PLA$_2$(Ca$^-$) can be prepared using standard methods for preparing polyclonal or monoclonal antibodies.

Scintillation Proximity Assay beads emit light when they are exposed to the radioactive energy from the tritiated arachidonic acid bound to the beads through the PLA$_2$(Ca$^-$) -antibody linkage, but the unreacted radioactive phosphatidylcholine in solution is too far from the bead to elicit light. The light from the beads will be measured in a liquid scintillation counter and will be a measure of the arachidonic acid transferred to the PLA$_2$(Ca$^-$).

Values from assays conducted with test inhibitory compounds will be compared to assays conducted with test compound diluent alone in order to ascertain inhibitory potency.

In an alternative assay, the PLA$_2$(Ca$^-$) will be d with tritiated phosphatidylcholine as above and the mixture will be treated with anti-PLA$_2$(Ca$^-$) antibody bound to Magnetic Beads (Advanced Magnetics, Cambridge, Mass., or Amersham, Arlington Heights, Ill.). The arachidonate-PLA$_2$(Ca$^-$) complex can then be separated from unreacted phosphatidylcholine by using a magnet to pellet the magnetic beads. The unreacted phosphatidylcholine would then be washed away to waste. The radioactivity in the retained beads can then be measured by conventional liquid scintillation counting.

PURIFICATION OF RECOMBINANT PLA$_2$(Ca$^-$)

If PLA$_2$(Ca$^-$) is expressed in a baculovirus/*Spodoptera frugiperda* system (see U.S. Pat. Nos. 4,745,051 and 4,879,236, and Summers and Smith "Manual of Methods for Baculovirus Vectors and Insect Cell Culture Procedures", 2nd edition, *Texas Agricultural Station Bulletin No.* 15555, Texas Agricultural Experiment Station, College Station, Texas), the recombinant polypeptide so produced can be purified by the following method.

The Sf9 cells containing recombinant PLA$_2$(Ca$^-$) are centrifuged and the cell pellet stored at $-80°$ C. in 50 ml plastic tubes prior to polypeptide purification. The cell pellets are resuspended in 20 ml of buffer A (50 mM Tris-Cl, pH 7.0, 1mM EGTA, 10% glycerol) at 4° C. and the cells broken by homogenization using a 50 ml glass homogenizer with teflon pestle. The cells are further disrupted by two thirty second bursts with a probe sonicator (Branson) using a microtip at 35% of maximum power. All subsequent purification steps are done at 4° C. The broken cells are centrifuged at 100,000×g for 60 min. and the supernatant is dialyzed against 100 volumes of buffer A for 6 hours or overnight.

The dialyzed supernatant is then loaded onto a DEAE-cellulose column (5.0×30 cm) previously equilibrated with buffer A. The PLA$_2$(Ca$^-$) activities are eluted with a 4 liter salt gradient (0–450 mM NaCl) in buffer A at a flow rate of 10 ml/min. The peak of PLA$_2$(Ca$^-$) activity eluting from the column at about 250 mM NaCl is collected (approximately 300 ml) and dialyzed against 30 volumes of buffer A at pH 8.0 for 4 hours. The dialysate is then concentrated by loading on a DEAE-cellulose "wide bore" column (1.6×2 cm) preequilibrated in buffer A at pH 8.0 and eluted with buffer A, pH 7.0 containing 410 mM NaCl. The concentrated PLA$_2$(Ca$^-$) is dialyzed against two changes of 10 volumes buffer C (50 mM HEPES, pH 7.4, 10% glycerol) for 4 hours. The dialyzate is loaded onto an HR 10/10 mono Q anion exchange column and the PLA$_2$(Ca$^-$) activity is eluted using a non-linear salt gradient (0–350 mM NaCl in buffer C). The peak of PLA$_2$(Ca$^-$) activity eluting from the Mono Q column is dialyzed against two changes of 100 volumes buffer C for 4 hours. The dialysate is made 1 mM in CHAPS (3-[(3-cholamidopropyl)-dimethylammonio]-1-propanesulfonate) and aliquoted into 1 ml plastic tubes before quick freezing in liquid nitrogen.

---

What is claimed is:

1. A purified nucleic acid molecule having a nucleotide sequence that encodes an amino acid sequence that comprises SEQ ID NO: 2.

2. The purified nucleic acid molecule according to claim 1 comprising the coding portion of SEQ ID NO: 1.

3. An expression vector comprising the nucleic acid molecule of claim 1.

4. An expression vector comprising the nucleic acid molecule of claim 2.

5. A transformed host cell comprising the expression vector of claim 3.

6. A transformed host cell comprising the expression vector of claim 4.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 853 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: CDS
        ( B ) LOCATION: 85..822

( x i ) SEQUENCE DESCRIPTION: SEQ ID NO:1:

```
GCCCACTCCC ACCGCCAGCT GGAACCCTGG GGACTACGAC GTCCCTCAAA CCTTGCTTCT        60

AGGAGATAAA AAGAACATCC AGTC ATG GAT AAA AAT GAG CTG GTT CAG AAG         111
                           Met Asp Lys Asn Glu Leu Val Gln Lys
                            1               5

GCC AAA CTG GCC GAG CAG GCT GAG CGA TAT GAT GAC ATG GCA GCC TGC        159
Ala Lys Leu Ala Glu Gln Ala Glu Arg Tyr Asp Asp Met Ala Ala Cys
 10              15                  20                  25

ATG AAG TCT GTA ACT GAG CAA GGA GCT GAA TTA TCC AAT GAG GAG AGG        207
Met Lys Ser Val Thr Glu Gln Gly Ala Glu Leu Ser Asn Glu Glu Arg
                 30                  35                  40

AAT CTT CTC TCA GTT GCT TAT AAA AAT GTT GTA GGA GCC CGT AGG TCA        255
Asn Leu Leu Ser Val Ala Tyr Lys Asn Val Val Gly Ala Arg Arg Ser
                 45                  50                  55

TCT TGG AGG GTC GTC TCA AGT ATT GAA CAA AAG ACG GAA GGT GCT GAG        303
Ser Trp Arg Val Val Ser Ser Ile Glu Gln Lys Thr Glu Gly Ala Glu
         60                  65                  70

AAA AAA CAG CAG ATG GCT CGA GAA TAC AGA GAG AAA ATT GAG ACG GAG        351
Lys Lys Gln Gln Met Ala Arg Glu Tyr Arg Glu Lys Ile Glu Thr Glu
 75                  80                  85

CTA AGA GAT ATC TGC AAT GAT GTA CTG TCT CTT TTG GAA AAG TTC TTG        399
Leu Arg Asp Ile Cys Asn Asp Val Leu Ser Leu Leu Glu Lys Phe Leu
 90                  95                 100                 105

ATC CCC AAT GCT TCA CAA GCA GAG AGC AAA GTC TTC TAT TTG AAA ATG        447
Ile Pro Asn Ala Ser Gln Ala Glu Ser Lys Val Phe Tyr Leu Lys Met
                110                 115                 120
```

| | | | | | | | | | | | | | | | | |
|---|---|---|---|---|---|---|---|---|---|---|---|---|---|---|---|---|
| AAA | GGA | GAT | TAC | TAC | CGT | TAC | TTG | GCT | GAG | GTT | GCC | GCT | GGT | GAT | GAC | 495 |
| Lys | Gly | Asp | Tyr 125 | Tyr | Arg | Tyr | Leu | Ala 130 | Glu | Val | Ala | Ala 135 | Gly | Asp | Asp | |
| AAG | AAA | GGG | ATT | GTC | GAT | CAG | TCA | CAA | CAA | GCA | TAC | CAA | GAA | GCT | TTT | 543 |
| Lys | Lys | Gly 140 | Ile | Val | Asp | Gln | Ser 145 | Gln | Gln | Ala | Tyr 150 | Gln | Glu | Ala | Phe | |
| GAA | ATC | AGC | AAA | AAG | GAA | ATG | CAA | CCA | ACA | CAT | CCT | ATC | AGA | CTG | GGT | 591 |
| Glu | Ile 155 | Ser | Lys | Lys | Glu | Met 160 | Gln | Pro | Thr | His | Pro 165 | Ile | Arg | Leu | Gly | |
| CTG | GCC | CTT | AAC | TTC | TCT | GTG | TTC | TAT | TAT | GAG | ATT | CTG | AAC | TCC | CCA | 639 |
| Leu 170 | Ala | Leu | Asn | Phe | Ser 175 | Val | Phe | Tyr | Tyr | Glu 180 | Ile | Leu | Asn | Ser | Pro 185 | |
| GAG | AAA | GCC | TGC | TCT | CTT | GCA | AAG | ACA | GCT | TTT | GAT | GAA | GCC | ATT | GCT | 687 |
| Glu | Lys | Ala | Cys | Ser 190 | Leu | Ala | Lys | Thr | Ala 195 | Phe | Asp | Glu | Ala | Ile 200 | Ala | |
| GAA | CTT | GAT | ACA | TTA | AGT | GAA | GAG | TCA | TAC | AAA | GAC | AGC | ACG | CTA | ATA | 735 |
| Glu | Leu | Asp | Thr 205 | Leu | Ser | Glu | Glu | Ser 210 | Tyr | Lys | Asp | Ser | Thr 215 | Leu | Ile | |
| ATG | CAA | TTA | CTG | AGA | GAC | AAC | TTG | ACA | TTG | TGG | ACA | TCG | GAT | ACC | CAA | 783 |
| Met | Gln | Leu 220 | Leu | Arg | Asp | Asn | Leu 225 | Thr | Leu | Trp | Thr | Ser 230 | Asp | Thr | Gln | |
| GGA | GAC | GAA | GCT | GAA | GCA | GGA | GAA | GGA | GGG | GAA | AAT | TAACCGGCCT | | | | 829 |
| Gly | Asp 235 | Glu | Ala | Glu | Ala 240 | Gly | Glu | Gly | Gly | Glu | Asn 245 | | | | | |

TCCAACTTTT GTCTGCCTCA TTCT  853

( 2 ) INFORMATION FOR SEQ ID NO:2:

( i ) SEQUENCE CHARACTERISTICS:
          ( A ) LENGTH: 245 amino acids
          ( B ) TYPE: amino acid
          ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Asp | Lys | Asn | Glu 5 | Leu | Val | Gln | Lys | Ala 10 | Lys | Leu | Ala | Glu | Gln Ala 15 |
| Glu | Arg | Tyr | Asp 20 | Asp | Met | Ala | Ala | Cys 25 | Met | Lys | Ser | Val | Thr 30 | Glu Gln |
| Gly | Ala | Glu 35 | Leu | Ser | Asn | Glu | Glu 40 | Arg | Asn | Leu | Leu | Ser 45 | Val | Ala Tyr |
| Lys | Asn 50 | Val | Val | Gly | Ala | Arg 55 | Arg | Ser | Ser | Trp | Arg 60 | Val | Val | Ser Ser |
| Ile 65 | Glu | Gln | Lys | Thr | Glu 70 | Gly | Ala | Glu | Lys | Lys 75 | Gln | Gln | Met | Ala Arg 80 |
| Glu | Tyr | Arg | Glu | Lys 85 | Ile | Glu | Thr | Glu | Leu 90 | Arg | Asp | Ile | Cys | Asn Asp 95 |
| Val | Leu | Ser | Leu 100 | Leu | Glu | Lys | Phe | Leu 105 | Ile | Pro | Asn | Ala | Ser 110 | Gln Ala |
| Glu | Ser | Lys 115 | Val | Phe | Tyr | Leu | Lys 120 | Met | Lys | Gly | Asp | Tyr 125 | Tyr | Arg Tyr |
| Leu | Ala 130 | Glu | Val | Ala | Ala | Gly 135 | Asp | Asp | Lys | Lys | Gly 140 | Ile | Val | Asp Gln |
| Ser 145 | Gln | Gln | Ala | Tyr | Gln 150 | Glu | Ala | Phe | Glu | Ile 155 | Ser | Lys | Lys | Glu Met 160 |
| Gln | Pro | Thr | His | Pro 165 | Ile | Arg | Leu | Gly | Leu 170 | Ala | Leu | Asn | Phe | Ser Val 175 |
| Phe | Tyr | Tyr | Glu 180 | Ile | Leu | Asn | Ser | Pro 185 | Glu | Lys | Ala | Cys | Ser 190 | Leu Ala |

```
Lys Thr Ala Phe Asp Glu Ala Ile Ala Glu Leu Asp Thr Leu Ser Glu
         195                 200                 205

Glu Ser Tyr Lys Asp Ser Thr Leu Ile Met Gln Leu Leu Arg Asp Asn
         210                 215                 220

Leu Thr Leu Trp Thr Ser Asp Thr Gln Gly Asp Glu Ala Glu Ala Gly
225                 230                 235                 240

Glu Gly Gly Glu Asn
                245
```

( 2 ) INFORMATION FOR SEQ ID NO:3:

( i ) SEQUENCE CHARACTERISTICS:
        ( A ) LENGTH: 121 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GTCTCAAGTA TTGAACAAAA GACGGAAGGT GCTGAGAAAA AACAGCAGAT GGCTCGAGAA      60

TACAGAGAGA AAATTCAGAC AGAGCTAAGA GATATCTGCA ATGATGTACT GTCTCTTTGG     120

G                                                                      121
```

( 2 ) INFORMATION FOR SEQ ID NO:4:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TCAAGTATTG AACAAAGAC GGAAGGTGCT GAGAAAAAAC AGCAGATGGC TCGAGAACAC       60

AGAGAGAAAA TTGAGACGGA GCTAAGAGAT ATCTGTAATG ATGTATTGTC TCTTTGGAA      120

AAGTTCTTGA TCCCCAATGC TTCACAAGCA GAGAGCAAAG TC                        162
```

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
TTCTGAATTC AGGAAACAGA CCATGGATAA AAATGAGCTG GTT                        43
```

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
AAGAGAATTC AGCTGGAAGC AGGTTTAATT TTCCCCTCCT TCTCC                      45
```

( 2 ) INFORMATION FOR SEQ ID NO:7:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO:7:

CAAAGTCTTC TATTGAA 17